United States Patent
Akao

(10) Patent No.: US 11,075,532 B2
(45) Date of Patent: Jul. 27, 2021

(54) POWER SUPPLY UNIT FOR AEROSOL INHALER, AND CONTROL METHOD AND CONTROL PROGRAM OF THE SAME

(71) Applicant: JAPAN TOBACCO INC., Tokyo (JP)

(72) Inventor: Takeshi Akao, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 35 days.

(21) Appl. No.: 16/668,793

(22) Filed: Oct. 30, 2019

(65) Prior Publication Data

US 2020/0136415 A1  Apr. 30, 2020

(30) Foreign Application Priority Data

Oct. 31, 2018  (JP) ............................. JP2018-204704

(51) Int. Cl.
 *H02J 7/00* (2006.01)
 *A24F 47/00* (2020.01)
 *A61M 15/00* (2006.01)
 *A24F 40/90* (2020.01)

(52) U.S. Cl.
 CPC ............ *H02J 7/0068* (2013.01); *A24F 40/90* (2020.01); *A24F 47/008* (2013.01); *A61M 15/009* (2013.01); *H02J 7/00* (2013.01); *A61M 2205/50* (2013.01); *A61M 2205/8206* (2013.01)

(58) Field of Classification Search
 CPC ............ A24F 47/008; A61M 2205/50; A61M 2205/8206; A61M 15/009; H02J 7/0068
 USPC ........................................................ 320/128
 See application file for complete search history.

(56) References Cited

U.S. PATENT DOCUMENTS

| | | | |
|---|---|---|---|
| 2002/0145402 A1 | 10/2002 | Ueda et al. | |
| 2008/0238356 A1 | 10/2008 | Batson et al. | |
| 2014/0014125 A1 | 1/2014 | Fernando et al. | |
| 2015/0181942 A1 | 7/2015 | Holzherr et al. | |
| 2015/0374040 A1* | 12/2015 | Chen ................... | G01R 31/66 131/328 |
| 2017/0150758 A1 | 6/2017 | Fernando et al. | |
| 2017/0302089 A1 | 10/2017 | Bernauer et al. | |
| 2020/0212517 A1* | 7/2020 | Akao et al. ............ | A24F 40/53 |

FOREIGN PATENT DOCUMENTS

| | | |
|---|---|---|
| JP | 2000-134819 A | 5/2000 |
| JP | 2002-315218 A | 10/2002 |
| JP | 2002-359009 A | 12/2002 |
| JP | 2006-50812 A | 2/2006 |

(Continued)

OTHER PUBLICATIONS

Communication dated Apr. 9, 2019, from the Japanese Patent Office in counterpart application No. 2018-204704.

(Continued)

*Primary Examiner* — Sun J Lin
(74) *Attorney, Agent, or Firm* — Sughrue Mion, PLLC

(57) ABSTRACT

A power supply unit for an aerosol inhaler includes: a power supply that is able to discharge power to a load for generating an aerosol from an aerosol generation source; and a control unit that is configured to determine whether the power supply which is being charged has reached a predetermined charge state lower than a fully charged state, and complete charging of the power supply in a case of determining that the power supply has reached the predetermined charge state.

7 Claims, 11 Drawing Sheets

(56) References Cited

FOREIGN PATENT DOCUMENTS

| | | | |
|---|---|---|---|
| JP | 2010-521947 | A | 6/2010 |
| JP | 2014-500017 | A | 1/2014 |
| JP | 2015-534458 | A | 12/2015 |
| JP | 2016-167915 | A | 9/2016 |
| JP | 2017-539191 | A | 12/2017 |
| JP | 2018-93877 | A | 6/2018 |
| WO | 2017055793 | A1 | 4/2017 |

OTHER PUBLICATIONS

Communication dated Nov. 20, 2018, from the Japanese Patent Office in counterpart application No. 2018-204704.

* cited by examiner

POWER SUPPLY UNIT FOR AEROSOL INHALER, AND CONTROL METHOD AND CONTROL PROGRAM OF THE SAME

CROSS-REFERENCE TO RELATED APPLICATIONS

This application is based upon and claims the benefit of priority from prior Japanese patent application No. 2018-204704, filed on Oct. 31, 2018, the entire contents of which are incorporated herein by reference.

TECHNICAL FIELD

The present invention relates to a power supply unit for an aerosol inhaler, and a control method and control program of the power supply unit.

BACKGROUND ART

There is available an aerosol inhaler which includes an aerosol generation source, a load for generating an aerosol from the aerosol generation source, a power supply able to discharge power to the load, and a control unit for controlling the power supply (see Patent Literatures 1 and 2 for instance).

Patent Literature 1: JP-A-2018-093877
Patent Literature 2: JP-A-2015-534458

Since an aerosol inhaler may be often used, it is desirable that it is possible to quickly charge a power supply of the aerosol inhaler.

An object of the present invention is to provide a power supply unit for an aerosol inhaler, and a control method and control program of the power supply unit, capable of making the aerosol inhaler useable by early completing charging of a power supply.

SUMMARY OF INVENTION

According to an aspect of the invention, there is provided a power supply unit for an aerosol inhaler, the power supply unit comprising: a power supply that is able to discharge power to a load for generating an aerosol from an aerosol generation source; and a control unit that is configured to determine whether the power supply which is being charged has reached a predetermined charge state lower than a fully charged state, and complete charging of the power supply in a case of determining that the power supply has reached the predetermined charge state.

DESCRIPTION OF EMBODIMENTS

Figure 1:
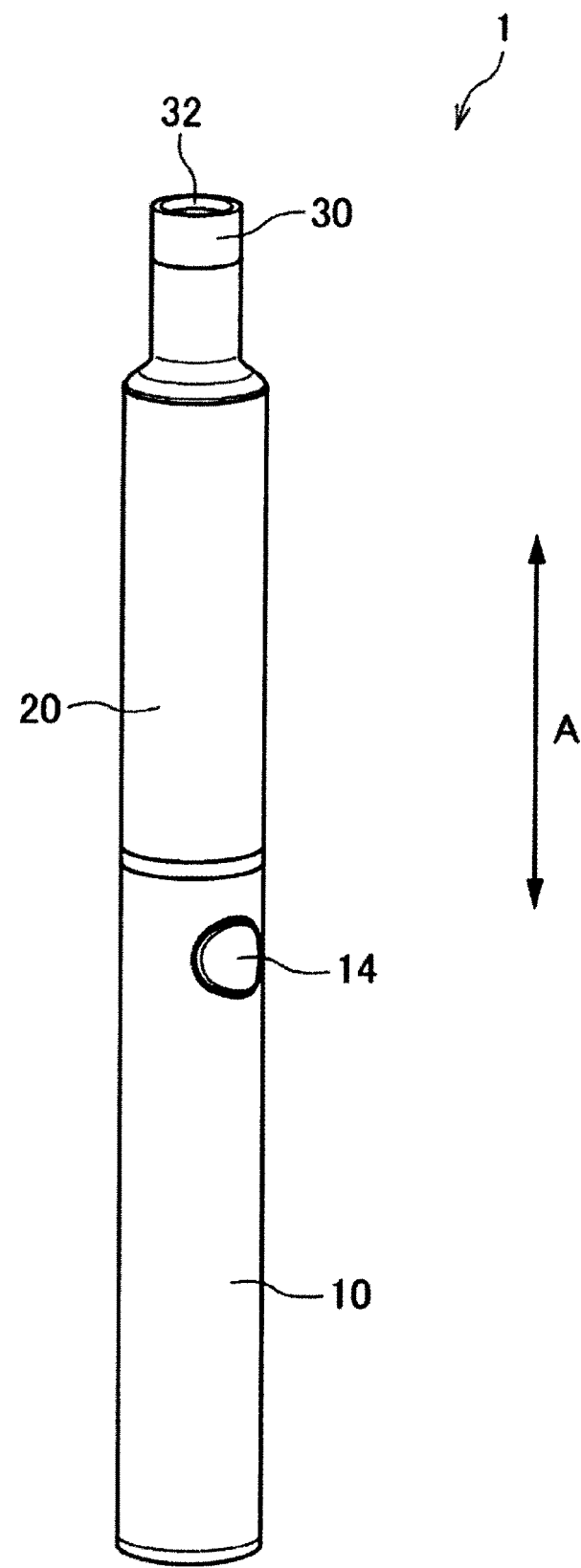
FIG. 1 is a perspective view of an aerosol inhaler equipped with a power supply unit of an embodiment of the present invention.
Figure 2:
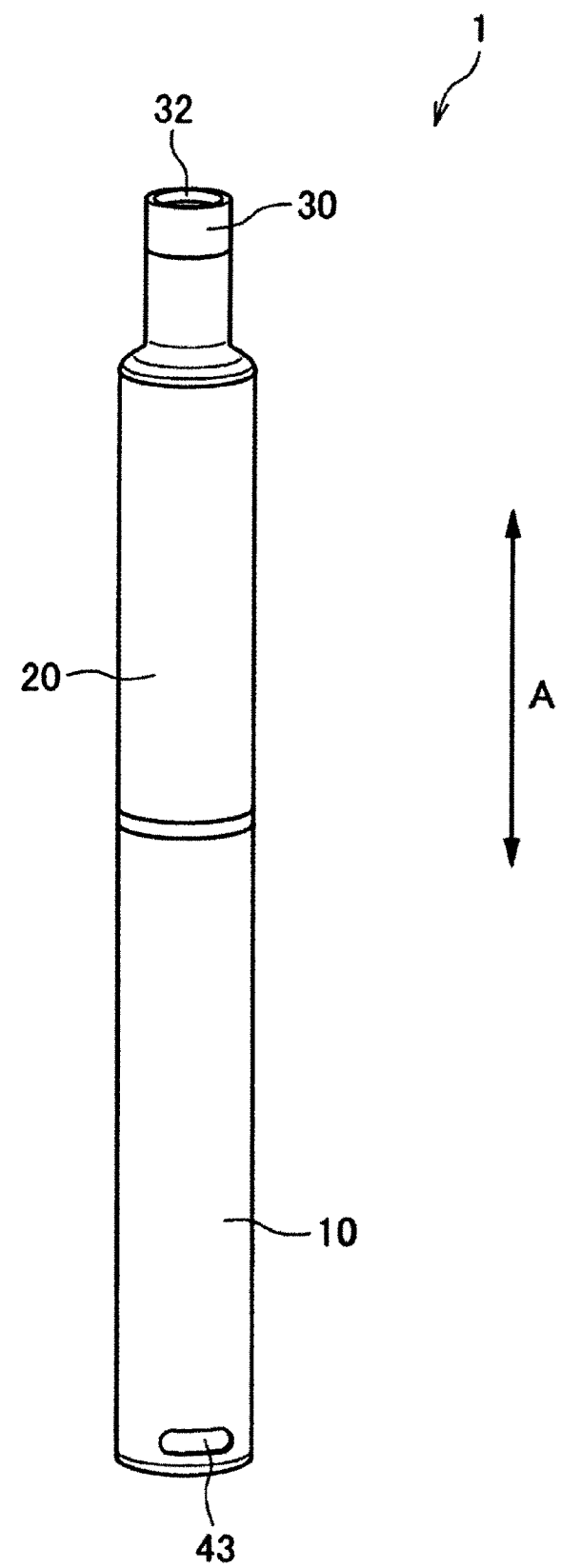
FIG. 2 is another perspective view of the aerosol inhaler of FIG. 1.

Hereinafter, a power supply unit for an aerosol inhaler according to an embodiment of the present invention will be described. First of all, the aerosol inhaler equipped with the power supply unit will be described with reference to FIG. 1 and FIG. 2.

(Aerosol Inhaler)

An aerosol inhaler 1 is a device for inhaling an aerosol containing a flavor without combustion, and has a rod shape extending along a certain direction (hereinafter, referred to as the longitudinal direction A). The aerosol inhaler 1 includes a power supply unit 10, a first cartridge 20, and a second cartridge 30 which are arranged in the order along the longitudinal direction A. The first cartridge 20 can be attached to and detached from the power supply unit 10. The second cartridge 30 can be attached to and detached from the first cartridge 20. In other words, the first cartridge 20 and the second cartridge 30 can be individually replaced.

(Power Supply Unit)

Figure 3:
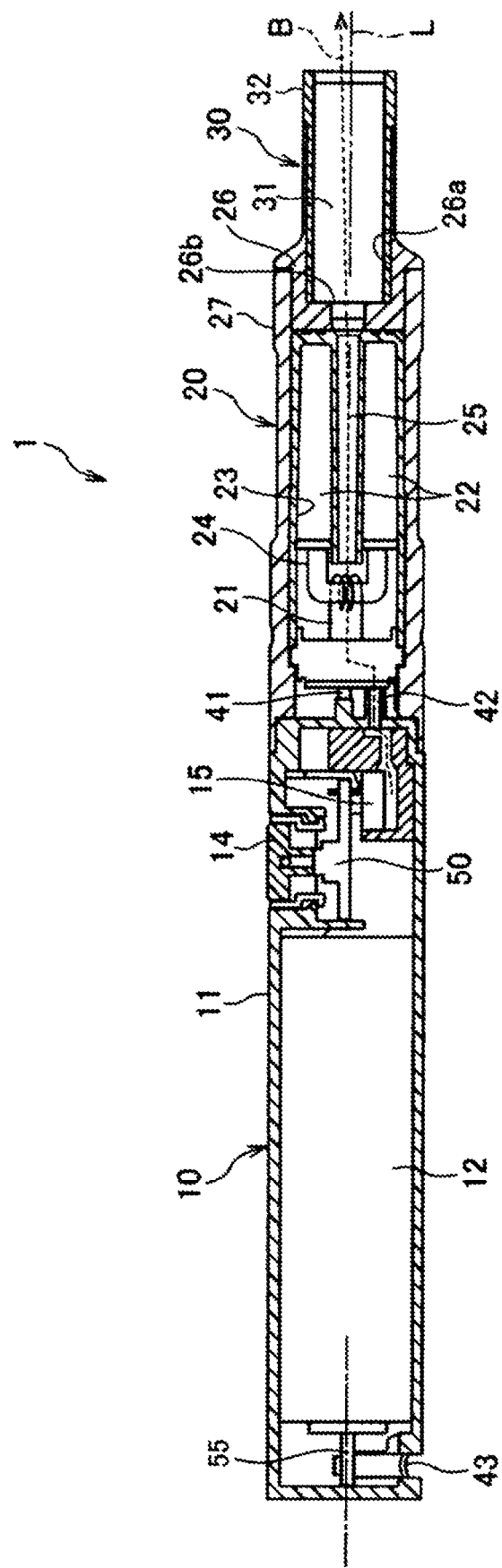
FIG. 3 is a cross-sectional view of the aerosol inhaler of FIG. 1.
Figure 4:
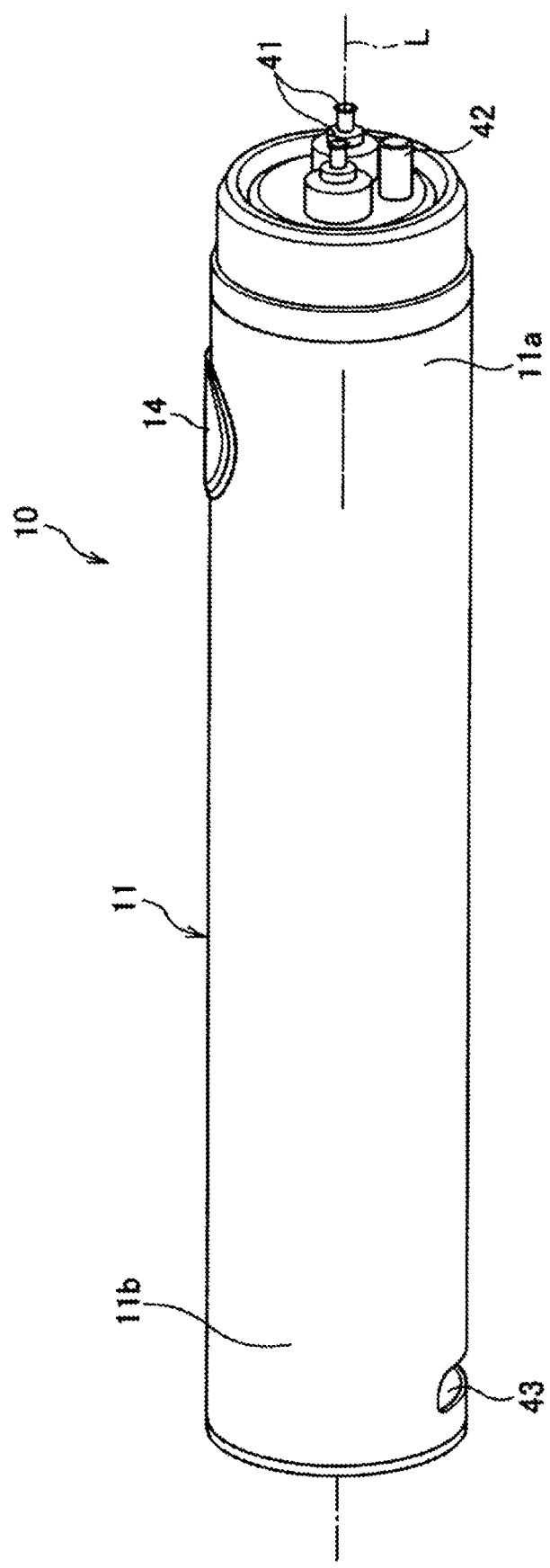
FIG. 4 is a perspective view of the power supply unit in the aerosol inhaler of FIG. 1.
Figure 6:
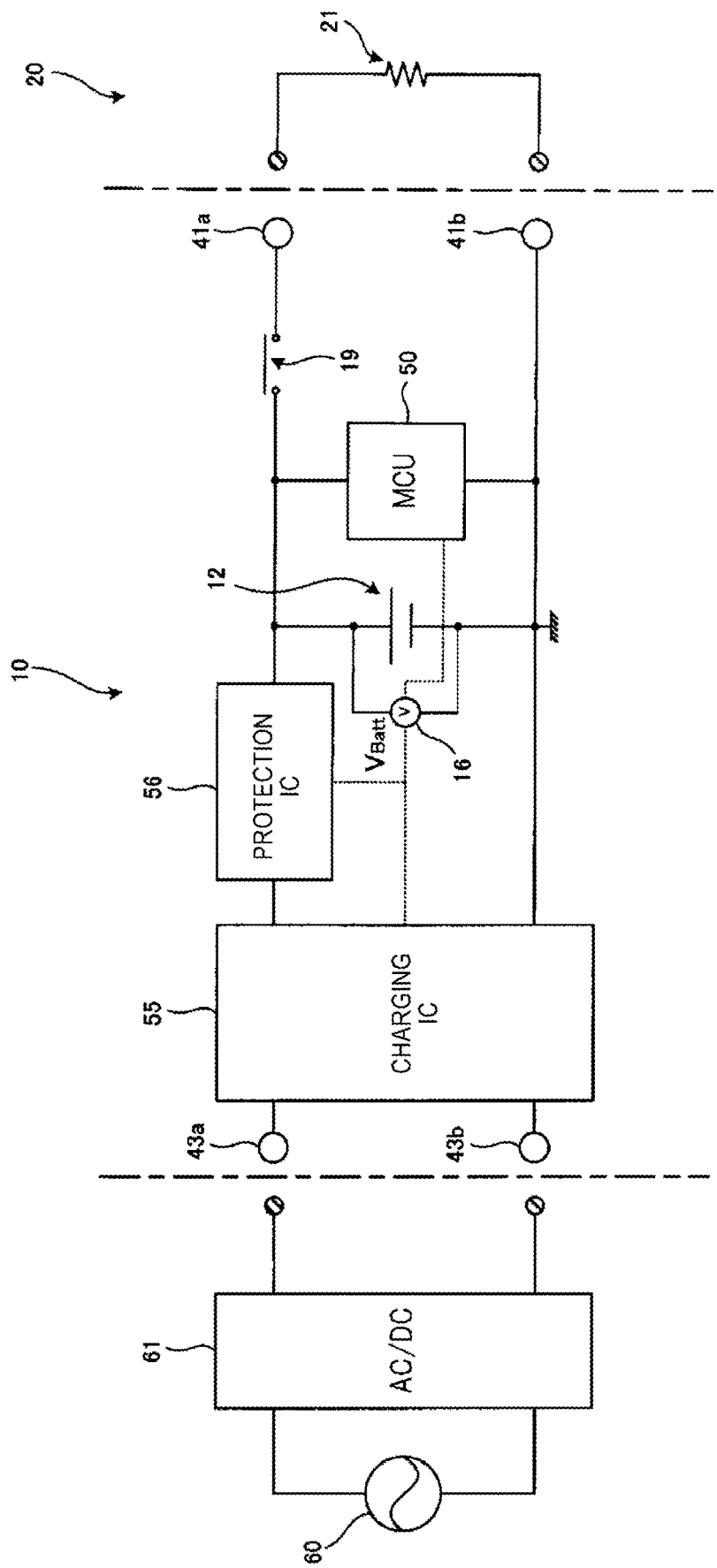
FIG. 6 is a schematic diagram illustrating the circuit configuration of the power supply unit in the aerosol inhaler of FIG. 6.

The power supply unit 10 of the present embodiment includes a power supply 12, a charging IC 55, a protection IC 56, an MCU 50, a switch 19, a voltage sensor 16, various sensors, and so on in a cylindrical power supply unit case 11, as shown in FIG. 3, FIG. 4, and FIG. 6. The power supply 12 is a chargeable secondary battery, an electric double-layer capacitor, or the like, and is preferably a lithium-ion battery.

On a top part 11a of the power supply unit case 11 positioned on one end side in the longitudinal direction A (the first cartridge (20) side), a discharging terminal 41 is provided. The discharging terminal 41 is provided so as to protrude from the top surface of the top part 11a toward the first cartridge 20, and is configured to be able to be electrically connected to a load 21 of the first cartridge 20.

Further, on a part of the top surface of the top part 11a in the vicinity of the discharging terminal 41, an air supply part 42 for supplying air to the load 21 of the first cartridge 20 is provided.

On a bottom part 11b of the power supply unit 10 positioned on the other end side in the longitudinal direction A (the opposite side to the first cartridge 20), a charging terminal 43 able to be electrically connected to an external power supply 60 (see FIG. 6) capable of charging the power supply 12 is provided. The charging terminal 43 is provided on the side surface of the bottom part 11b, such that, for example, at least one of USB terminals, micro USB terminals, and Lightning terminals can be connected thereto. However, the charging terminal 43 may be a power receiving part able to receive power from the external power supply 60 in a non-contact manner.

In this case, the charging terminal 43 (the power receiving part) may be composed of a power receiving coil. The wireless power transfer system may be an electromagnetic induction type, or may be a magnetic resonance type. Also, the charging terminal 43 may be a power receiving part able to receive power from the external power supply 60 without any contact point. As another example, the charging terminal 43 may be configured such that at least one of USB terminals, micro USB terminals, and Lightning terminals can be connected thereto and the above-mentioned power receiving part is included therein.

On the side surface of the top part 11a of the power supply unit case 11, an operation unit 14 which the user can operate is provided so as to face the opposite side to the charging terminal 43. More specifically, the operation unit 14 and the charging terminal 43 are symmetric with respect to the point of intersection of a straight line connecting the operation unit 14 and the charging terminal 43 and the center line of the power supply unit 10 in the longitudinal direction A. The operation unit 14 is composed of a button type switch, a touch panel, or the like. In the vicinity of the operation unit 14, an inhalation sensor 15 for detecting a puff action are provided.

The charging IC 55 is disposed close to the charging terminal 43, and performs control on charging of the power supply 12 with power which is input from the charging terminal 43. The charging IC 55 includes a converter for converting direct current, which is applied from an inverter 61 or the like provided for converting alternating current into direct current on a charging cable which is connected to the charging terminal, into direct current having a different parameter, a voltmeter for measuring charging voltage $V_{CHG}$ which is supplied from the converter to the power supply 12, an ammeter for measuring charging current $I_{CHG}$ which is supplied from the converter to the power supply 12, a processor for controlling them, and so on. In this specification, the processor is more specifically an electric circuit configured by combining circuit elements such as semiconductor elements.

The charging IC 55 selectively performs constant current charging (CC charging) for charging the power supply 12 by performing control such that the charging current $I_{CHG}$ becomes constant, and constant voltage charging (CV charging) for charging the power supply 12 by performing control such that the charging voltage $V_{CHG}$ becomes constant. The charging IC 55 charges the power supply 12 by CC charging, in the state where power-supply voltage $V_{Batt}$ corresponding to the amount of power stored in the power supply 12 is lower than a predetermined CV switch voltage, and charges the power supply 12 by CV charging, in the state where the power-supply voltage $V_{Batt}$ is equal to or higher than the above-mentioned CV switch voltage.

Figure 5:
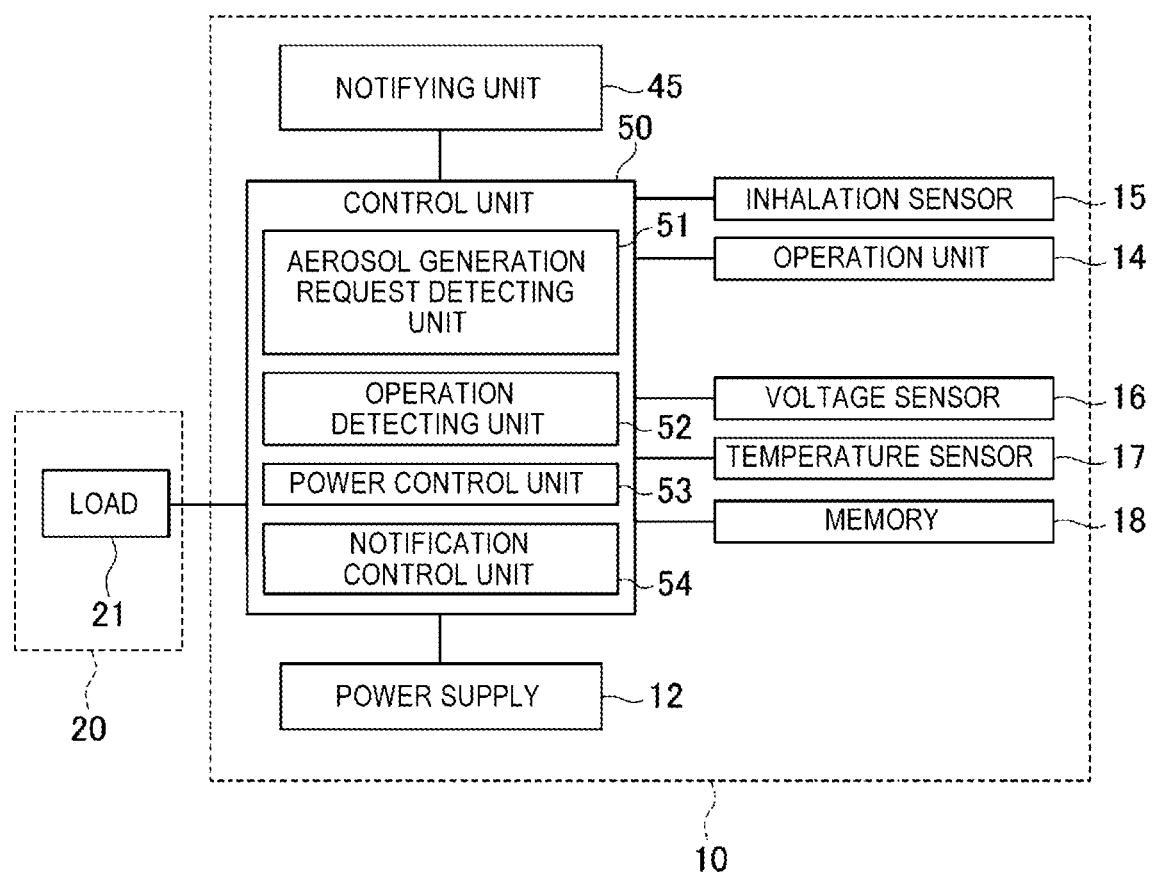
FIG. 5 is a block diagram illustrating the main part configuration of the power supply unit in the aerosol inhaler of FIG. 1.

The MCU 50 is connected to various sensor devices, such as the inhalation sensor 15 for detecting a puff (inhaling) action, a voltage sensor 16 for measuring the power-supply voltage $V_{Batt}$ of the power supply 12, and a temperature sensor 17 for measuring the temperature of the power supply 12, the operation unit 14, a notifying unit 45 (to be described below), and a memory 18 for storing the number of puff actions, the time for which power has been applied to the load 21, as shown in FIG. 5, and performs a variety of control on the aerosol inhaler 1. The MCU 50 is specifically a processor.

Also, in the power supply unit case 11, an air intake (not shown in the drawings) for taking in air is formed. The air intake may be formed around the operation unit 14, or may be formed around the charging terminal 43.

(First Cartridge)

As shown in FIG. 3, the first cartridge 20 includes a reservoir 23 for storing an aerosol source 22, the electric load 21 for atomizing the aerosol source 22, a wick 24 for drawing the aerosol source from the reservoir 23 toward the load 21, an aerosol channel 25 for an aerosol generated by atomizing the aerosol source 22 to flow toward the second cartridge 30, an end cap 26 for storing a part of the second cartridge 30.

The reservoir 23 is formed so as to surround the aerosol channel 25, and holds the aerosol source 22. In the reservoir 23, a porous member such as a resin web or cotton may be stored, and the porous member may be impregnated with the aerosol source 22. The aerosol source 22 includes a liquid such as glycerin, propylene glycol, or water.

The wick 24 is a liquid holding member for drawing the aerosol source 22 toward the load 21 using capillarity, and is configured with, for example, glass fiber, a porous ceramic, or the like.

The load 21 atomizes the aerosol source 22 without combustion by power which is supplied from the power supply 12 through the discharging terminal 41. The load 21 is configured with a heating wire wound with a predetermined pitch (a coil). However, the load 21 needs only to be an element capable of atomizing the aerosol source 22, thereby generating an aerosol, and is, for example, a heating element or an ultrasonic wave generator. Examples of the heating element include a heating resistor, a ceramic heater, an induction heating type heater, and so on.

The aerosol channel 25 is provided on the downstream side of the load 21 on the center line L of the power supply unit 10.

The end cap 26 includes a cartridge storage part 26a for storing a part of the second cartridge 30, and a connecting passage 26b for connecting the aerosol channel 25 and the cartridge storage part 26a.

(Second Cartridge)

The second cartridge 30 holds a flavor source 31. The end part of the second cartridge 30 on the first cartridge (20) side is stored in the cartridge storage part 26a provided in the end cap 26 of the first cartridge 20, so as to be able to be removed. The end part of the second cartridge 30 on the opposite side to the first cartridge (20) side is configured as an inhalation port 32 for the user. However, the inhalation port 32 does not necessarily need to be configured integrally with the second cartridge 30 so as not to be separable from the second cartridge, and may be configured to be able to be attached to and detached from the second cartridge 30. If the inhalation port 32 is configured separately from the power supply unit 10 and the first cartridge 20 as described above, it is possible to keep the inhalation port 32 sanitary.

The second cartridge 30 adds a flavor to the aerosol generated by atomizing the aerosol source 22 by the load 21, by passing the aerosol through the flavor source 31. As a raw material piece which constitutes the flavor source, a compact made by forming shredded tobacco or a tobacco raw material into a grain shape can be used. The flavor source 31 may be configured with a plant (such as mint or a herbal medicine, or a herb) other than tobacco. To the flavor source 31, a flavoring agent such as menthol may be added.

The aerosol inhaler 1 of the present embodiment can generate an aerosol containing the flavor by the aerosol source 22, the flavor source 31, and the load 21. In other words, the aerosol source 22 and the flavor source 31 constitute an aerosol generation source for generating an aerosol.

The aerosol generation source in the aerosol inhaler 1 is a part which the user can replace to use. For this part, for example, one first cartridge 20 and one or more (for example, five) second cartridges 30 can be provided as one set to the user.

The configuration of the aerosol generation source which can be used in the aerosol inhaler 1 is not limited to the configuration in which the aerosol source 22 and the flavor source 31 are configured separately, and may be a configuration in which the aerosol source 22 and the flavor source 31 are formed integrally, a configuration in which the flavor source 31 is omitted and the aerosol source 22 contains a substance which can be contained in the flavor source 31, a configuration in which the aerosol source 22 contains a medical substance or the like instead of the flavor source 31, or the like.

For an aerosol inhaler 1 including an aerosol generation source configured by integrally forming an aerosol source 22 and a flavor source 31, for example, one or more (for example, 20) aerosol generation sources may be provided as one set to the user.

In the case of an aerosol inhaler 1 including only an aerosol source 22 as an aerosol generation source, for example, one or more (for example, 20) aerosol generation sources may be provided as one set to the user.

In the aerosol inhaler 1 configured as described above, as shown by an arrow B in FIG. 3, air entering from the intake (not shown in the drawings) formed in the power supply unit case 11 passes through the air supply part 42, and passes near the load 21 of the first cartridge 20. The load 21 atomizes the aerosol source 22 drawn from the reservoir 23 by the wick 24. The aerosol generated by atomizing flows through the aerosol channel 25 together with the air entering from the intake, and is supplied to the second cartridge 30 through the connecting passage 26b. The aerosol supplied to the second cartridge 30 passes through the flavor source 31, whereby the flavor is added, and is supplied to the inhalation port 32.

Also, in the aerosol inhaler 1, a notifying unit 45 for notifying a variety of information is provided (see FIG. 5). The notifying unit 45 may be configured with a light emitting element, or may be configured with a vibrating element, or may be configured with a sound output element. The notifying unit 45 may be a combination of two or more elements of light emitting elements, vibrating elements, and sound output elements. The notifying unit 45 may be provided in any one of the power supply unit 10, the first cartridge 20, and the second cartridge 30; however, it is preferable that the notifying unit be provided in the power supply unit 10. For example, the area around the operation unit 14 is configured to have translucency to permit light which is emitted by a light emitting element such as an LED to pass through.

(Electronic Circuit)

Now, the details of the electric circuit of the power supply unit 10 will be described with reference to FIG. 6.

The power supply unit 10 includes the power supply 12, a positive electrode side discharging terminal 41a and a negative electrode side discharging terminal 41b which constitute the discharging terminal 41, a positive electrode side charging terminal 43a and a negative electrode side charging terminal 43b which constitute the charging terminal 43, the MCU (Micro Controller Unit) 50 which is connected between the positive electrode side of the power supply 12 and the positive electrode side discharging terminal 41a and between the negative electrode side of the power supply 12 and the negative electrode side discharging terminal 41b, the charging IC 55 which is disposed on the power transmission path between the charging terminal 43 and the power supply 12, the protection IC 56 which is disposed on the power transmission path between the charging IC 55 and the power supply 12, and a switch 19 which is disposed on the power transmission path between the power supply 12 and the discharging terminal 41.

The switch 19 is configured with, for example, a semiconductor element such as a MOSFET, and is opened and closed by control of the MCU 50. The MCU 50 has a function of detecting that the external power supply 60 is connected to the charging terminal 43, on the basis of variation in the voltage between the MCU and the charging terminal 43.

In the electric circuit of the power supply unit 10 shown in FIG. 6, the switch 19 is provided between the positive electrode side of the power supply 12 and the positive electrode side discharging terminal 41a. Instead of this so-called plus control type, the switch 19 may be a minus control type which is provided between the negative electrode side discharging terminal 41b and the negative electrode side of the power supply 12.

In the case where the power supply 12 is being charged by the charging IC 55, the protection IC 56 monitors the power-supply voltage $V_{Batt}$ measured by the voltage sensor 16, and in the case where the power-supply voltage $V_{Batt}$ reaches a protection voltage threshold (hereinafter, as an example, it is assumed that the protection voltage threshold is 4.275 V), the protection IC shuts off the power transmission path extending from the charging IC 55 to the power supply 12, thereby stopping charging of the power supply 12 in order to protect the power supply 12 from overcharging or overcurrent. If the power transmission path extending from the charging IC 55 to the power supply 12 is shut off by the protection IC 56, the charging IC 55 ends charging of the power supply 12.

(MCU)

Now, the configuration of the MCU 50 will be described in more detail.

As shown in FIG. 5, the MCU 50 includes an aerosol generation request detecting unit 51, an operation detecting unit 52, a power control unit 53, and a notification control unit 54 as functional blocks.

The aerosol generation request detecting unit 51 detects a request for aerosol generation on the basis of the output result of the inhalation sensor 15. The inhalation sensor 15 is configured to output the value of a variation in the pressure in the power supply unit 10 (the internal pressure) caused by inhalation of the user through the inhalation port 32. The inhalation sensor 15 is, for example, a pressure sensor for outputting an output value (for example, a voltage value or a current value) according to the internal pressure which varies according to the flow rate of air which is sucked from the intake (not shown in the drawings) toward the inhalation port 32 (i.e. a puff action of the user). The inhalation sensor 15 may be configured with a capacitor microphone or the like.

The operation detecting unit 52 detects an operation which is performed on the operation unit 14 by the user.

The notification control unit 54 controls the notifying unit 45 such that the notifying unit notifies a variety of information. For example, the notification control unit 54 controls the notifying unit 45 in response to detection of a timing to replace the second cartridge 30, such that the notifying unit notifies the timing to replace the second cartridge 30. The notification control unit 54 detects and notifies a timing to replace the second cartridge 30, on the basis of the number of puff actions and the cumulative time for which power has been supplied to the load 21, stored in the memory 18. The notification control unit 54 is not limited to notification of a timing to replace the second cartridge 30, and may notify a timing to replace the first cartridge 20, a timing to replace the power supply 12, a timing to charge the power supply 12, and so on.

In the state where one unused second cartridge 30 is set, if a predetermined number of puff actions are performed, or if the cumulative time for which power has been applied to the load 21 due to puff actions reaches a predetermined value (for example, 120 seconds), the notification control unit 54 determines that the second cartridge 30 is used up (i.e. the remaining amount is zero or the second cartridge is empty), and notifies the timing to replace the second cartridge 30.

Also, in the case of determining that all of the second cartridges 30 included in one set are used up, the notification control unit 54 may determine that one first cartridge 20 included in the single set is used up (i.e. the remaining amount is zero or the first cartridge is empty), and notify the timing to replace the first cartridge 20.

Also, the notification control unit 54 calculates the state of charge (SOC) which is a numerical index indicating the ratio of the amount of power stored in the power supply 12 (the amount of stored power) to the capacity of the power supply 12, and controls the notifying unit 45 such that the notifying unit notifies the calculated SOC.

The notification control unit 54 determines, for example, which of a first range equal to or larger than 0% and smaller than 33%, a second range equal to or larger than 33% and smaller than 66%, and a third range equal to or larger than 66% and smaller than 100% the SOC belongs to. Further, depending on the case where the SOC is in the first range, the case where the SOC is in the second range, and the case where the SOC is in the third range, the notification control unit 54 performs control, for example, turning on or flashing light emitting elements included in the notifying unit 45 in different colors, turning on or flashing light emitting elements included in the notifying unit 45 in different patterns, changing the number of light emitting elements to be turned on or flashed, of a plurality of light emitting elements included in the notifying unit 45, changing the output sound of a sound output element of the notifying unit 45, or changing the vibration pattern of a vibrating element of the notifying unit 45. Therefore, the user of the aerosol inhaler 1 can intuitively the magnitude of the SOC of the power supply 12 by sound, color, or vibration, not by characters or an image which is displayed on a display or the like.

If the notification control unit 54 notifies the SOC in the above-mentioned way, even if early charging completion control to be described below is performed, as compared to the case of directly displaying the value of the SOC, it is possible to effectively reduce a feeling of strangeness which the user feels.

The power control unit 53 controls discharging of the power supply 12 through the discharging terminal 41 by switching on and off the switch 19 if the aerosol generation request detecting unit 51 detects the request for aerosol generation.

The power control unit 53 performs control such that the amount of aerosol which is generated by atomizing the aerosol source by the load 21 falls in a desired range, i.e. such that the amount of power which is supplied from the power supply 12 to the load 21 falls in a predetermined range. Specifically, the power control unit 53 controls switching on and off of the switch 19 by, for example, PWM (Pulse Width Modulation) control. Alternatively, the power control unit 53 may control switching on and off of the switch 19 by PFM (Pulse Frequency Modulation) control.

The power control unit 53 stops supply of power from the power supply 12 to the load 21 if a predetermined period passes after start of supply of power to the load 21. In other words, even while the user is actually performing a puff action, if the puff period exceeds a certain period, the power control unit 53 stops supply of power from the power supply 12 to the load 21. The certain period is determined to suppress variation in user's puff period.

By control of the power control unit 53, the current which flows in the load 21 during one puff action becomes substantially a constant value which is determined according to substantially constant effective voltage which is supplied to the load 21 by PWM control, and the resistance values of the discharging terminal 41 and the load 21. In the aerosol inhaler 1 of the present embodiment, when the user inhales an aerosol using one unused second cartridge 30, the cumulative time for which power can be supplied to the load 21 is controlled to a maximum of, for example, 120 seconds. Therefore, in the case where one first cartridge 20 and five second cartridges 30 constitute one set, it is possible to obtain the maximum amount of power required to empty (use up) the single set, in advance.

Also, the power control unit 53 detects an electric connection between the charging terminal 43 and the external power supply 60.

In the above-mentioned CV charging, in theory, charging is kept until the charging voltage $V_{CHG}$ and the power-supply voltage $V_{Batt}$ become equal. As the power-supply voltage $V_{Batt}$ approaches the charging voltage $V_{CHG}$, power which is stored in the power supply 12 steps down. Therefore, it takes a very long time for the charging voltage $V_{CHG}$ and the power-supply voltage $V_{Batt}$ to become strictly equal. For this reason, in general CV charging, charging is considered to be completed when charging current becomes equal to or smaller than a threshold. However, sometimes, due to an error of a sensor which detects voltage or current, or setting of a threshold, it takes a long time for charging to be considered to be completed.

For this reason, the power control unit 53 also performs control for stopping (completing) charging of the power supply 12 in the case where a predetermined condition is satisfied in the state where charging of the power supply 12 is being performed by the charging IC 55.

The power supply unit 10 configured as described above determines whether the power supply 12 which is being charged from the external power supply 60 has reached a predetermined charge state lower than the fully charged state (for example, a range in which the SOC is between 80% and 96%, or a range in which the SOC between 80% and 90%, or the like), and completes charging of the power supply 12 in the case of determining that the charge state of the power supply 12 has reached the predetermined charge state. For example, when it is assumed that the full charging voltage of the power supply 12 (the power-supply voltage when the SOC is 100%) is 4.2 V, if the power supply unit 10 determines that the power-supply voltage $V_{Batt}$ has become, for example, about 4.06 V, the power supply unit 10 completes charging of the power supply 12. In this way, the time required until charging is completed is shortened.

By the way, the power-supply voltage $V_{Batt}$ and the SOC have a correlation. In the case where it is determined that the power-supply voltage $V_{Batt}$ has become, for example, about 4.06 V, if charging of the power supply 12 is completed, the SOC becomes about 85% to 96%.

The charging IC 55 and the MCU 50 are configured to determine whether the charge state of the power supply 12 has reached the predetermined charge state, using different determination conditions, respectively. As a result, the accuracy of determination improves, and the probability of completing charging of the power supply 12 before the power supply 12 becomes the fully charged state increases. Also, it becomes possible to complete charging of the power supply 12 before the power supply 12 becomes the fully charged state, even in the case where one of the charging IC 55 and the MCU 50 does not normally operate.

Also, the predetermined charge state is a state where the amount of power equal to or larger than the amount of power required to be supplied to the load 21 in order to empty one set or two sets of unused aerosol generation sources which are provided to the user is stored in the power supply 12. Therefore, even in the state where charging of the power supply 12 has been completed before the power supply becomes the fully charged state, it is possible to use up one set or two sets of aerosol generation sources.

For example, it is assumed that current to flow in the load 21 during discharging of the power supply 12 is set to 1.44 A and the maximum of cumulative time for which power is supplied to the load 21 for each second cartridge 30 is controlled to 120 seconds. In this case, the maximum amount of power necessary to empty one set becomes 240 mAh, and the maximum amount of power necessary to empty two sets becomes 480 mAh. As the power supply 12, a large-capacity power supply is used such that the SOC becomes smaller than 100% when the amount of stored power is, for example, 480 mAh or a value larger than 480 mAh by a small margin (for example, 510 mAh or 540 mAh).

(Power Supply Charging Operation)

Figure 7:
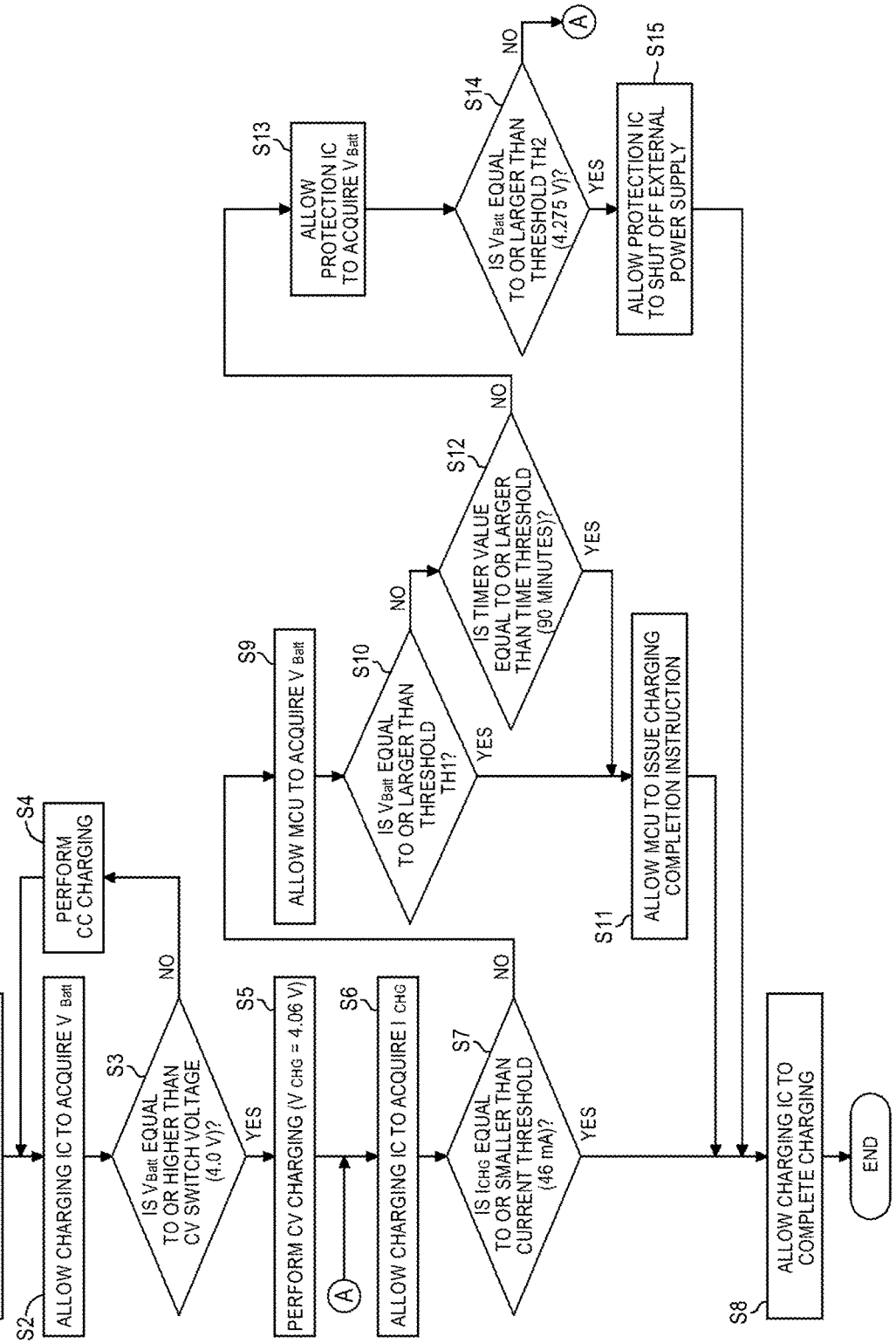
FIG. 7 is a flow chart for explaining a power supply charging operation of the power supply unit shown in FIG. 6.
Figure 8:
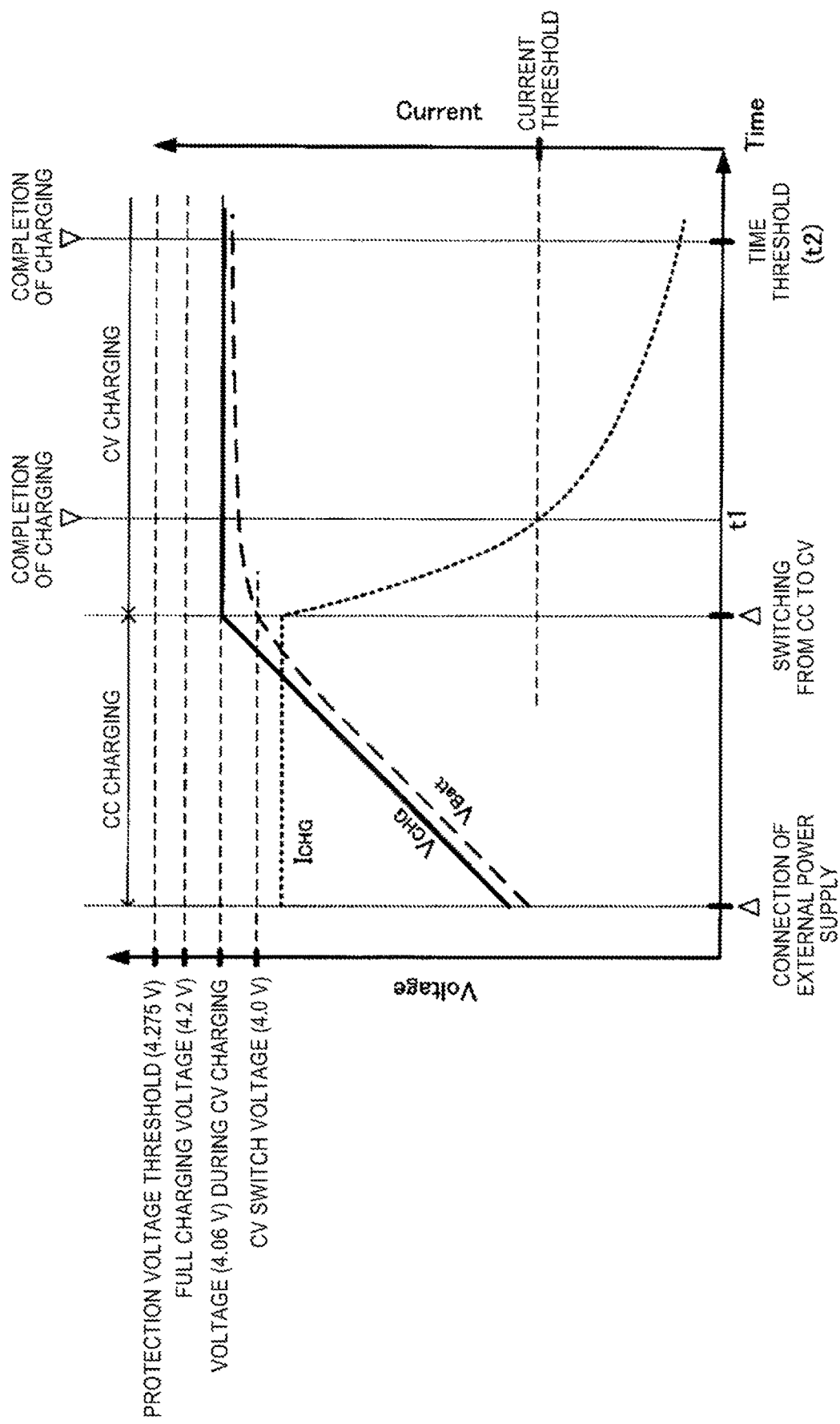
FIG. 8 is a view for explaining the charging operation shown in FIG. 7.

FIG. 7 is a flow chart for explaining the operation of the power supply unit 10 during charging of the power supply 12. FIG. 8 is a view illustrating examples of the temporal transitions of the charging voltage $V_{CHG}$, the charging current $I_{CHG}$, and the power-supply voltage $V_{Batt}$ during charging of the power supply 12.

If the MCU 50 detects an electric connection between the charging terminal 43 and the external power supply 60, the operation shown in FIG. 7 is started. Hereinafter, as an example, the case where the full charging voltage of the power supply 12 is 4.2 V and the above-mentioned CV switch voltage is 4.0 V will be described. Further, on the assumption that a power supply 12 having full charge capacity of 610 mAh is used and charging is completed if 540 mAh is stored in the power supply 12, the following description will be made. In this case, the predetermined charge state is the state where the SOC is 89%. Also, in this operation, some or all of processes which are performed by each of the MCU 50 and the charging IC 55 can be performed according to a program by a processor.

First of all, the MCU 50 activates a built-in timer (STEP S1). Next, the charging IC 55 acquires the power-supply voltage $V_{Batt}$ from the voltage sensor 16 (STEP S2), and determines whether the power-supply voltage $V_{Batt}$ is equal to or higher than the CV switch voltage, or not (STEP S3). If the power-supply voltage $V_{Batt}$ is lower than the CV switch voltage ("NO" in STEP S3), the charging IC 55 starts charging of the power supply 12 by CC charging (STEP S4), and then returns to STEP S2. While the power-supply voltage $V_{Batt}$ is lower than the CV switch voltage, the processes of STEP S1 to STEP S4 are repeated, and the power supply 12 is quickly charged by CC charging.

Then, if the power-supply voltage $V_{Batt}$ reaches the CV switch voltage ("YES" in STEP S3), the charging IC 55 starts charging of the power supply 12 by CV charging in which the charging voltage $V_{CHG}$ has a value larger than the value of the CV switch voltage (preferably, power-supply voltage, i.e. 4.06 V, corresponding to the predetermined charge state in which the SOC is 89%) (STEP S5).

If CV charging is started in STEP S5, the charging IC 55 acquires the charging current $I_{CHG}$ from the internal ammeter, and determines whether the charging current $I_{CHG}$ is equal to or smaller than a current threshold (in the example of FIG. 7, 46 mA), or not (STEP S7). This current threshold was a threshold determined by starting CV charging from a state where power-supply voltage was 4.0 V under predetermined conditions (such as atmospheric temperature, the temperature of the power supply 12, and so on) and actually measuring change of the charging current $I_{CHG}$, and is such a value that it is possible to determine that the SOC is 89% if the charging current $I_{CHG}$ becomes the corresponding value.

If the charging current $I_{CHG}$ is equal to or smaller than the current threshold ("YES" in STEP S7), the charging IC 55 determines that the charge state of the power supply 12 has reached the predetermined charge state, i.e. the SOC of 89%, and stops supply of power from the external power supply 60 to the power supply 12, thereby completing charging of the power supply 12 (STEP S8, a time t1 of FIG. 8).

In the case where it is determined in STEP S7 that the charging current $I_{CHG}$ exceeds the current threshold ("NO" in STEP S7), the charging IC 55 determines that the SOC of the power supply 12 has not reached 89%, and keeps the CV charging. By the way, the curve showing the change of the charging current $I_{CHG}$ after the start of the CV charging as shown in FIG. 8 also changes according to the atmospheric temperature in the place where the power supply unit 10 is placed and the temperature of the power supply 12. Also, the measurement value of the charging current $I_{CHG}$ also can change according to measurement errors of various sensors, aging of various sensors, and so on. For this reason, even through the SOC actually reaches 89%, the determination in STEP S7 may become "NO".

For this reason, in this case, the MCU 50 acquires the power-supply voltage $V_{Batt}$ from the voltage sensor 16 (STEP S9), and determines whether the power-supply voltage $V_{Batt}$ is equal to or larger than a threshold TH1, or not (STEP S10). As the threshold TH1, the power-supply voltage, i.e. 4.06 V, corresponding to the SOC of 89% is set. However, it is preferable that a value (for example, 4.2 V or the like) obtained by adding a certain voltage to the power-supply voltage, i.e. 4.06 V, be set as the threshold TH1 in consideration of an error of the voltage sensor 16 and so on.

In the case where the power-supply voltage $V_{Batt}$ is equal to or larger than the threshold TH1 ("YES" in STEP S10), the MCU 50 determines that the SOC of the power supply 12 has become 89% or greater, and instructs the charging IC 55 to complete the charging (STEP S11). If receiving this instruction, the charging IC 55 stops supply of power from the external power supply 60 to the power supply 12, thereby completing the charging of the power supply 12, in STEP S8. Alternatively, in the circuit configuration of FIG. 6, a switch (not shown in the drawings) provided between the charging IC 55 and the power supply 12 may be turned off to forcibly stop supply of power from the external power supply 60 to the power supply 12.

In the case where the power-supply voltage $V_{Batt}$ is smaller than the threshold TH1 ("NO" in STEP S10), the MCU 50 determines whether the timer value of the built-in timer has reached a predetermined time threshold (in the example of FIGS. 7 and 8, 90 minutes) (STEP S12). In the case where the timer value has reached the time threshold ("YES" in STEP S12), the MCU 50 determines that the SOC of the power supply 12 has reached 89%, and instructs the charging IC 55 to complete the charging (STEP S11). By this process of STEP S11, as shown in FIG. 8, even though the charging is not completed at the time t1, at a time t2, the charging is completed before the power supply becomes the fully charged state.

As the time threshold, for example, a value obtained by adding a certain margin to the time taken for the SOC to become 89% by CV charging when the CV charging was started from the state where the SOC was 0% (the time actually measured during manufacturing) can be set. Since the time which is required to charge the power supply 12 tends to shorten as deterioration progresses, if the time which is obtained during manufacturing is used as a reference, in any deteriorated state or healthy state, it is possible to surely complete charging of the power supply 12.

In the case where the timer value has not reached the time threshold ("NO" in STEP S12), the MCU 50 determines that the SOC of the power supply 12 has not reach 89%. In this case, the protection IC 56 acquires the power-supply voltage $V_{Batt}$ from the voltage sensor 16 (STEP S13), and determines whether the power-supply voltage $V_{Batt}$ is equal to or larger than a threshold TH2, or not (STEP S14). The threshold TH2 is a value necessary to protect the power supply 12 from overcharging or overcurrent, and is set to a value larger than the full charging voltage.

In the case where the power-supply voltage $V_{Batt}$ has reached the threshold TH2 ("YES" in STEP S14), the protection IC 56 shuts off the power transmission path extending from the external power supply 60 to the power supply 12 (STEP S15). After STEP S15, in STEP S8, charging is completed. In the case where the power-supply voltage $V_{Batt}$ has not reached the threshold TH2 ("NO" in STEP S14), the process is shifted to STEP S6.

Effects of Embodiment

As described above, according to the power supply unit 10, since it is possible to complete charging of the power supply 12 before the power supply 12 becomes the fully charged state, quick charging requiring a shorter time until completion of charging becomes possible. Also, whether the power supply 12 is in the predetermined charge state lower than the fully charged state is determined by each of three different conditions, i.e. the condition on the charging current $I_{CHG}$ (the condition that the charging current $I_{CHG}$ should be equal to or larger than the current threshold), the condition on the power-supply voltage $V_{Batt}$ (the condition that the power-supply voltage $V_{Batt}$ should be equal to or larger than the threshold TH1), and the condition on the charging time which is the elapsed time from start of charging (the condition that the timer value should be equal to or larger than the time threshold). Therefore, it is possible to improve the accuracy of the determination, and it is possible to raise the probability that charging of the power supply 12 is forcibly completed before the power supply 12 becomes the fully charged state.

Also, the charging IC 55 and the MCU 50 perform the above-mentioned determination in cooperation with each other. Therefore, as compared to the case of performing the determination by only the charging IC 55 or the case of performing the determination by only the MCU 50, or other cases, it is possible to use a charging IC and an MCU having lower performance as the charging IC 55 and the MCU 50, respectively. Therefore, it is possible to reduce the manufacturing cost of the power supply unit 10. Especially, during charging of the power supply 12, the MCU 50 is not required to perform control for discharging of power to the load 21, so it has a margin in capacity. Therefore, efficient distributed processing becomes possible, and it is possible to improve the processing efficiency of the entire power supply unit 10.

Also, as compared to an embodiment in which charging of the power supply 12 is completed by only CC charging to be described below, since CV charging is performed after CC charging, it is possible to reduce the SOC of the power supply 12 and voltage variation at the time of completion of charging (First Modification of Charging Operation of Power Supply Unit)

The MCU 50 may change the time threshold to be compared with the timer value in STEP S12 of FIG. 7. Specifically, the MCU 50 changes the time threshold according to the ambient temperature of the power supply 12 acquired from the temperature sensor 17. In the case where the temperature of the power supply 12 is low, the charging time which is required until the power supply reaches a desired power-supply voltage is long. For this reason, it is preferable that in the case where the temperature is equal to or lower than a predetermined threshold, the MCU 50 set the time threshold to a larger value as compared to the case where the temperature exceeds the predetermined threshold. In this case, it is possible to further improve the accuracy of determination on the charge state of the power supply 12.

Also, the MCU 50 may change the time threshold according to the SOH (State Of Health) which is an index including the healthy state or deteriorated state of the power supply 12. As described above, the time which is required to charge the power supply 12 tends to shorten as deterioration progresses. For this reason, it is preferable to set the temperature threshold shorter as deterioration of the power supply 12 progresses. In this case, it is possible to further improve the accuracy of determination on the charge state of the power supply 12.

(Second Modification of Charging Operation of Power Supply Unit)

Figure 9:
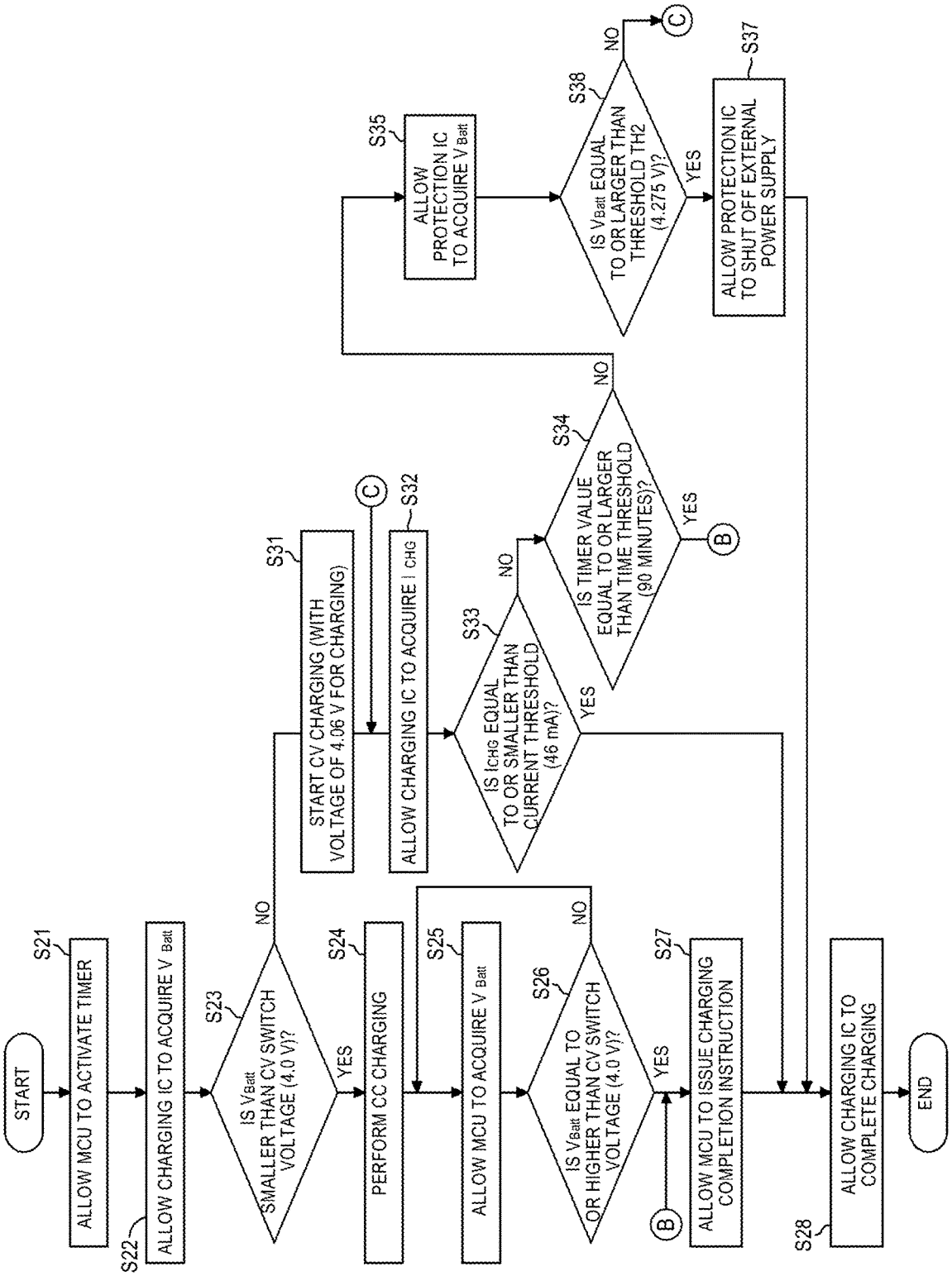
FIG. 9 is a flow chart for explaining a modification of the power supply charging operation of the power supply unit shown in FIG. 6.
Figure 10:
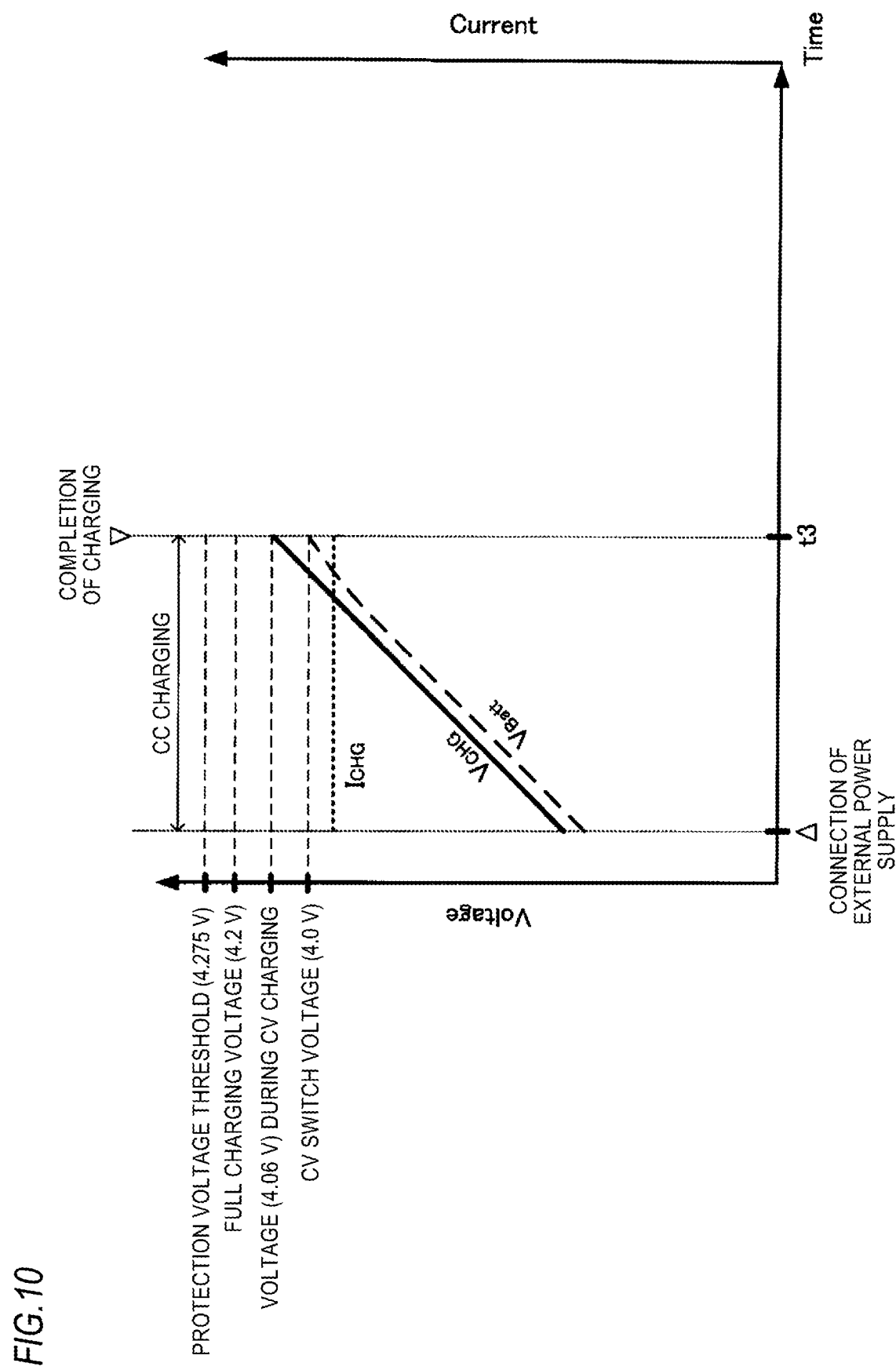
FIG. 10 is a view for explaining the charging operation shown in FIG. 9.
Figure 11:
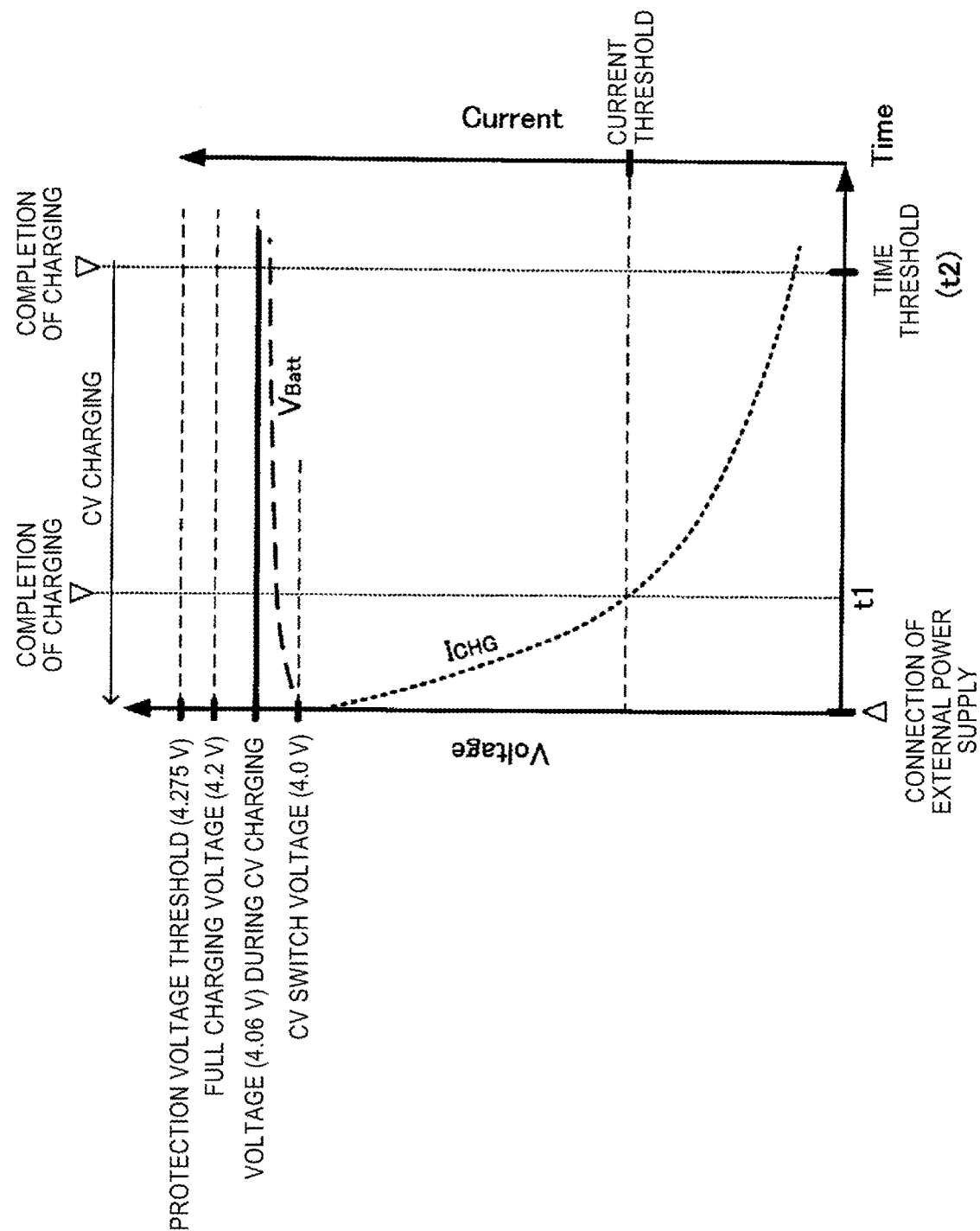
FIG. 11 is a view for explaining the charging operation shown in FIG. 9.

FIG. 9 is a flow chart for explaining a modification of the operation of the power supply unit 10 during charging of the power supply 12. FIG. 10 and FIG. 11 are views illustrating examples of the temporal transitions of the charging voltage $V_{CHG}$, the charging current $I_{CHG}$, and the power-supply voltage $V_{Batt}$ a during the operation shown in FIG. 9.

If the MCU 50 detects an electric connection between the charging terminal 43 and the external power supply 60, the operation shown in FIG. 9 is started. Hereinafter, as an example, the case where the full charging voltage of the power supply 12 is 4.2 V and the above-mentioned CV switch voltage is 4.0 V will be described. Further, on the assumption that a power supply 12 having full charge capacity of 610 mAh is used and charging is completed if 500 mAh is stored in the power supply 12, the following description will be made. In this case, the predetermined charge state is the state where the SOC is 82%.

First of all, the MCU 50 activates the built-in timer (STEP S21). Next, the charging IC 55 acquires the power-supply voltage $V_{Batt}$ from the voltage sensor 16 (STEP S22), and determines whether the power-supply voltage $V_{Batt}$ is lower than the CV switch voltage (STEP S23). If the power-supply voltage $V_{Batt}$ is lower than the CV switch voltage ("YES" in STEP S23), the charging IC 55 starts charging of the power supply 12 by CC charging (STEP S24). Examples of the transitions of the voltage and the current when STEP S24 is performed are shown in FIG. 10.

If CC charging is started, the MCU 50 acquires the power-supply voltage $V_{Batt}$ from the voltage sensor 16 (STEP S25), and determines whether the power-supply voltage $V_{Batt}$ is equal to or higher than the CV switch voltage, or not (STEP S26). In the case where the power-supply voltage $V_{Batt}$ is equal to or higher than the CV switch voltage ("YES" in STEP S26), the MCU 50 determines that the SOC of the power supply 12 has reached 82%, and instructs the charging IC 55 to complete the charging (STEP S27). If receiving this instruction, the charging IC 55 stops supply of power from the external power supply 60 to the power supply 12, thereby completing charging of the power supply 12, in STEP S28 (a time t3 of FIG. 10).

In the case where it is determined in STEP S23 that the power-supply voltage $V_{Batt}$ is equal to or higher than the CV switch voltage ("NO" in STEP S23), the charging IC 55 starts charging of the power supply 12 by CV charging with the charging voltage $V_{CHG}$ set to a value (preferably, 4.06 V which is the power-supply voltage corresponding to the SOC of 82%) larger than the CV switch voltage (STEP S31). Examples of the transitions of the voltage and the current when STEP S31 is performed are shown in FIG. 11.

If the CV charging is started in STEP S31, the charging IC 55 acquires the charging current $I_{CHG}$ from the internal ammeter (STEP S32), and determines whether the charging current $I_{CHG}$ is equal to or smaller than the current threshold (in the example of FIG. 9, 46 mA) (STEP S33).

If the charging current $I_{CHG}$ is equal to or smaller than the current threshold ("YES" in STEP S33), the charging IC 55 determines that the charge state of the power supply 12 has reached the SOC of 82%, and stops supply of power from the external power supply 60 to the power supply 12, thereby completing charging of the power supply 12 (STEP S28, a time t1 of FIG. 11).

In the case where it is determined in STEP S33 that the charging current $I_{CHG}$ exceeds the current threshold ("NO" in STEP S33), the charging IC 55 determines that the SOC of the power supply 12 has not reached 82%, and keeps the CV charging. Also, in this case, the MCU 50 determines whether the timer value of the built-in timer has reached the predetermined time threshold (in the examples of FIG. 9 and FIG. 11, 90 minutes) (STEP S34).

In the case where the timer value has reached the time threshold ("YES" in STEP S34), the MCU 50 determines that the SOC of the power supply 12 has reached 82%, and shifts the process to STEP S27. By this process of STEP S27, as shown in FIG. 11, even though the charging is not completed at the time t1, at a time t2, the charging is completed before the power supply becomes the fully charged state.

In the case where the timer value has not reached the time threshold ("NO" in STEP S34), the MCU 50 determines that the SOC of the power supply 12 has not reach 82%. In this case, the protection IC 56 acquires the power-supply voltage $V_{Batt}$ from the voltage sensor 16 (STEP S35), and determines whether the power-supply voltage $V_{Batt}$ is equal to or larger than a threshold TH2, or not (STEP S36).

In the case where the power-supply voltage $V_{Batt}$ has reached the threshold TH2 ("YES" in STEP S36), the protection IC 56 shuts off the power transmission path extending from the external power supply 60 to the power supply 12 (STEP S37). After STEP S37, in STEP S28, charging is completed. In the case where the power-supply voltage $V_{Batt}$ has not reached the threshold TH2 ("NO" in STEP S36), the process is shifted to STEP S32.

According to the operation of the second modification described above, if the power-supply voltage is lower than the CV switch voltage, charging of the power supply 12 is performed only by CC charging, and before the power supply reaches the fully charged state, the charging is completed. Therefore, even in the state where the amount of power stored in the power supply 12 is small, it is possible to shorten the time which is required until completion of charging, and it is possible to raise user satisfaction.

Also, even in the case where the power-supply voltage is equal to or higher than the CV switch voltage, by the processes of STEP S33 and STEP S34, it is possible to complete charging before the power supply becomes the fully charged state. Therefore, it is possible to shorten the time which is required until completion of charging, and it is possible to raise user satisfaction.

In this specification, at least the following inventions (1) to (19) are disclosed.

(1) A power supply unit for an aerosol inhaler, the power supply unit comprising:

a power supply that is able to discharge power to a load for generating an aerosol from an aerosol generation source; and a control unit that is configured to determine whether the power supply which is being charged has reached a predetermined charge state lower than a fully charged state, and complete charging of the power supply in a case of determining that the power supply has reached the predetermined charge state.

According to (1), it becomes possible to complete charging before the power supply reaches the fully charged state. Therefore, it is possible to early complete charging. Also, since the power supply does not become the fully charged state, it is possible to suppress deterioration of the power supply, and it is possible to extend the life of the power supply unit.

(2) The power supply unit according to (1), wherein the control unit charges the power supply by constant current charging, and in a case of determining that the power supply which is being charged by the constant current charging has reached the predetermined charge state, the control unit ends the constant current charging, thereby completing the charging of the power supply.

According to (2), since it is possible to complete charging of the power supply only by constant current charging, it is possible to shorten the charging time.

(3) The power supply unit according to (1), wherein the control unit charges the power supply by constant voltage charging, and in a case of determining that the power supply which is being charged by the constant voltage charging has reached the predetermined charge state, the control unit ends the constant voltage charging, thereby completing the charging of the power supply.

According to (3), since it is possible to perform charging by constant voltage charging until the power supply becomes the predetermined charge state, it is possible to stabilize the voltage of the power supply when the charging is completed.

(4) The power supply unit according to (3), wherein the control unit charges the power supply by constant current charging in a state where an voltage of the power supply is smaller than a first value smaller than a full charging voltage, and charges the power supply by the constant voltage charging using a voltage having a second value larger than the first value as supply voltage for the power supply, in a state where the voltage of the power supply reaches the first value.

According to (4), since charging is performed by the constant voltage charging until the power supply becomes the predetermined charge state, it is possible to stabilize the voltage of the power supply when the charging is completed. Also, even if charging is performed two or more times, it is possible to suppress variation in the voltage or SOC of the power supply when the charging is completed.

(5) The power supply unit according to (4), wherein the second value is smaller than the full charging voltage.

According to (5), since the constant voltage charging is performed with the voltage lower than the full charging voltage, accurate charging becomes possible.

(6) The power supply unit according to any one of (1) to (5), wherein:
the control unit completes the charging of the power supply in a case where any one of a plurality of conditions for determining that the power supply has reached the predetermined charge state is satisfied.

According to (6), since it is possible to determine the timing to complete the charging, according to the plurality of conditions, it is possible to raise the probability that the charging is forcibly completed before the power supply reaches the fully charged state.

(7) The power supply unit according to (6), wherein the plurality of conditions includes a condition on a charging current of the power supply, and a condition on a voltage of the power supply.

According to (7), since it is possible to determine the timing to complete the charging according to the plurality of conditions related to different physical amounts, it is possible to raise the probability that the charging is forcibly completed before the power supply reaches the fully charged state.

(8) The power supply unit according to (7), wherein the plurality of conditions includes a condition on a charging time of the power supply.

According to (8), since it also is possible to determine the timing to complete the charging according to the condition related to the charging time, it is possible to raise the probability that the charging is forcibly completed before the power supply reaches the fully charged state.

(9) The power supply unit according to any one of (6) to (8), wherein
the control unit includes a first control unit and a second control unit which individually determine whether the power supply has reached the predetermined charge state based on the conditions, and complete the charging of the power supply.

According to (9), it is possible to perform the determination for completing the charging in parallel by the first control unit and the second control unit. Therefore, it is possible to raise the probability that the charging is forcibly completed before the power supply reaches the fully charged state. Also, since it becomes unnecessary to use expensive units as the control unit as compared to the case of performing the determination by one control unit, it is possible to reduce the manufacturing cost.

(10) The power supply unit according to (9), wherein the first control unit and the second control unit perform the determination based on the different conditions.

According to (10), it is possible to perform determination for completing charging on the basis of different determination criteria in parallel by the first control unit and the second control unit. Therefore, it is possible to raise the probability that the charging is forcibly completed before the power supply reaches the fully charged state.

(11) The power supply unit according to (9) or (10), wherein
the first control unit is a circuit for performing control on the charging of the power supply, and
the second control unit is a circuit for performing control on discharge of power of the power supply to the load.

According to (11), it is possible to perform determination for completing charging by the second control unit having a margin in capacity during charging. Therefore, it is possible to distribute the load on the individual control units.

(12) The power supply unit according to (11), further including:
a protection circuit that is configured to protect the power supply.

According to (12), even through a state where it is impossible to complete charging although the power supply has reached the full charging voltage occurs, it is possible to protect the power supply. Therefore, it is possible to secure safety while performing quick charging.

(13) The power supply unit according to any one of (1) to (12), wherein
the predetermined charge state is a state where power equal to or larger than an amount of power required to be applied to the load in order to empty the aerosol generation source which is unused is stored in the power supply.

According to (13), if charging of the power supply is completed, it becomes possible to use up the aerosol generation source by the aerosol inhaler. Therefore, it is possible to prevent frequent charging of the power supply, thereby suppressing deterioration of the power supply.

(14) The power supply unit according to any one of (1) to (13), further comprising:
a notifying unit that is configured to notify an amount of power stored in the power supply by an element other than an element for displaying a character or an image.

According to (14), the amount of power stored in the power supply can be notified by, for example, the color, light emission pattern, or the like of the light emitting element. Therefore, even though charging of the power supply is completed by control of the control unit before the power supply becomes the fully charged state, it is possible to prevent a feeling of strangeness from being given to the user.

(15) A power supply unit for an aerosol inhaler, the power supply unit comprising:
a power supply that is able to discharge power to a load for generating an aerosol from an aerosol generation source:
a first control unit that is configured to perform control on charging of the power supply; and
a second control unit that is configured to perform control on discharge of power of the power supply to the load,
wherein each of the first control unit and the second control unit completes charging of the power supply in a case where any one of a plurality of conditions is satisfied.

According to (15), since it is possible to determine the timing to complete charging according to the plurality of conditions, it is possible to raise the probability that the charging is forcibly completed in a state where the power supply has reached the desired charge state.

(16) A control method of a power supply unit for an aerosol inhaler, the power supply unit including a power supply that is able to discharge power to a load for generating an aerosol from an aerosol generation source, the control method comprising:
a control step of determining whether the power supply has reached a predetermined charge state lower than a fully charged state, during charging of the power supply, and completing the charging of the power supply in a case of determining that the power supply has reached the predetermined charge state.

(17) A control program of a power supply unit for an aerosol inhaler, the power supply unit including a power supply that is able to discharge power to a load for generating an aerosol from an aerosol generation source, the control program making a computer execute:

a control step of determining whether the power supply has reached a predetermined charge state lower than a fully charged state, during charging of the power supply, and completing the charging of the power supply in a case of determining that the power supply has reached the predetermined charge state.

(18) A control method of a power supply unit for an aerosol inhaler, the power supply unit including a power supply that is able to discharge power to a load for generating an aerosol from an aerosol generation source, a first control unit that is configured to perform control on charging of the power supply, and a second control unit that is configured to perform control on discharge of power of the power supply to the load, the control method comprising:

causing the first control unit to execute control for completing the charging of the power supply in a case where any one of a plurality of conditions is satisfied, and causing the second control unit to execute control for completing the charging of the power supply in a case where any one of the plurality of conditions is satisfied,

(19) A control program of a power supply unit for an aerosol inhaler, the power supply unit including a power supply that is able to discharge power to a load for generating an aerosol from an aerosol generation source, a first control unit that is configured to perform control on charging of the power supply, and a second control unit that is configured to perform control on discharge of power of the power supply to the load, the control program comprising:

causing the first control unit to execute control for completing charging of the power supply in a case where any one of a plurality of conditions is satisfied, and causing the second control to execute control for completing charging of the power supply in a case where any one of the plurality of conditions is satisfied.

According to (16) to (19), it becomes possible to complete charging before the power supply reaches the fully charged state. Therefore, it is possible to early complete charging. Also, since the power supply does not become the fully charged state, it is possible to suppress deterioration of the power supply, and it is possible to extend the life of the power supply unit.

According to (1), and (15) to (19), it becomes possible to complete charging before the power supply reaches the fully charged state. Therefore, it is possible to early complete charging. Also, since the power supply does not become the fully charged state, it is possible to suppress deterioration of the power supply, and it is possible to extend the life of the power supply unit. Therefore, there is energy saving effect in which it is possible to use the power supply for a long time without replacing with a brand new one.

According to the present invention, it is possible to make an aerosol inhaler usable by early completing charging of a power supply.

What is claimed is:

1. A power supply unit for an aerosol inhaler, the power supply unit comprising:

a power supply that is able to discharge power to a load for generating an aerosol from an aerosol generation source; and a control unit that is configured to determine whether the power supply which is being charged has reached a predetermined charge state lower than a fully charged state, and complete charging of the power supply in a case of determining that the power supply has reached the predetermined charge state, wherein the control unit includes a first control unit and a second control unit which individually determine whether the power supply has reached the predetermined charge state based on a plurality of conditions for determining that the power supply has reached the predetermined charge state, and complete the charging of the power supply, the first control unit is a circuit for performing a control on the charging of the power supply, and the second control unit is a circuit for performing a control on the discharging of power of the power supply to the load.

2. The power supply unit according to claim 1, wherein the plurality of conditions include a condition on a charging current of the power supply, and a condition on a voltage of the power supply.

3. The power supply unit according to claim 2, wherein the plurality of conditions include a condition on a charging time of the power supply.

4. The power supply unit according to claim 1, wherein the first control unit and the second control unit perform the determination based on different conditions of the plurality of conditions.

5. A power supply unit for an aerosol inhaler, the power supply unit comprising: a power supply that is able to discharge power to a load for generating an aerosol from an aerosol generation source;

a first control unit that is configured to perform a control on charging of the power supply;
and a second control unit that is configured to perform a control on discharging of power of the power supply to the load, wherein each of the first control unit and the second control unit respectively completes the charging of the power supply and the discharging of the power supply to the load in a case where any condition of a plurality of conditions is satisfied.

6. A control method of a power supply unit for an aerosol inhaler, the power supply unit including a power supply that is able to discharge power to a load for generating an aerosol from an aerosol generation source, a first control unit that is configured to perform a control on charging of the power supply, and a second control unit that is configured to perform a control on discharge of power of the power supply to the load, the control method comprising:

causing the first control unit to execute a control for completing the charging of the power supply in a case where any condition of the plurality of conditions is satisfied, and causing the second control unit to execute a control for completing the discharging of the power supply to the load in a case where any condition of the plurality of conditions is satisfied.

7. A non-transitory computer-readable recording medium in which a control program of a power supply unit for an aerosol inhaler is recorded, the control program causing a computer to execute the control method according to claim 6.

* * * * *